United States Patent
Sarjoui et al.

(10) Patent No.: US 10,531,275 B2
(45) Date of Patent: Jan. 7, 2020

(54) CLUSTER NEIGHBOR DISCOVERY IN CENTRALIZED RADIO ACCESS NETWORK USING TRANSPORT NETWORK LAYER (TNL) ADDRESS DISCOVERY

(71) Applicant: CommScope Technologies LLC, Hickory, NC (US)

(72) Inventors: Fatemeh Fazel Sarjoui, Somerville, MA (US); Nagi Jayaraman Mahalingam, Windham, NH (US)

(73) Assignee: CommScope Technologies LLC, Hickory, NC (US)

( * ) Notice: Subject to any disclaimer, the term of this patent is extended or adjusted under 35 U.S.C. 154(b) by 0 days.

(21) Appl. No.: 15/839,656

(22) Filed: Dec. 12, 2017

(65) Prior Publication Data

US 2018/0167803 A1 Jun. 14, 2018

Related U.S. Application Data

(60) Provisional application No. 62/433,013, filed on Dec. 12, 2016.

(51) Int. Cl.
*H04W 36/00* (2009.01)
*H04W 8/14* (2009.01)
(Continued)

(52) U.S. Cl.
CPC .......... *H04W 8/14* (2013.01); *H04L 61/2015* (2013.01); *H04L 61/256* (2013.01);
(Continued)

(58) Field of Classification Search
CPC ......... H04W 8/14; H04W 8/00; H04W 88/08; H04W 8/26; H04W 8/005; H04W 92/20;
(Continued)

(56) References Cited

U.S. PATENT DOCUMENTS

2009/0042597 A1* 2/2009 Yuuki .................. H04W 76/12
455/525
2010/0124228 A1* 5/2010 Tinnakornsrisuphap ...................
H04W 76/12
370/392
(Continued)

FOREIGN PATENT DOCUMENTS

WO 2015113640 A1 8/2015

OTHER PUBLICATIONS

"3GPP TS 36.423 v14.0.0", "Technical Specification", Dated Sep. 30, 2016, pp. 1-239, Release 14, Publisher: 3GPP Organizational Partners.
(Continued)

*Primary Examiner* — Khoi H Tran
*Assistant Examiner* — B M M Hannan
(74) *Attorney, Agent, or Firm* — Fogg & Powers LLC

(57) ABSTRACT

A request is sent from a first base station to a second base station for a transport layer address assigned to the second base station that is suitable for establishing a connection between the first base station and the second base station. The second base station determines whether to include an outer address assigned to the second base station in a response to the request. If that is the case, the second base station sends the response to the first base station that includes a tunnel inner address assigned by a security gateway to the second base station and the outer address. The first base station determines whether the outer address is included in the response. If that is case, the outer address is used to establish the connection between the first base station and the second base station without using the security gateway.

33 Claims, 6 Drawing Sheets

(51) Int. Cl.
*H04L 29/08* (2006.01)
*H04W 8/00* (2009.01)
*H04W 92/20* (2009.01)
*H04L 29/12* (2006.01)
*H04W 8/26* (2009.01)
*H04W 88/08* (2009.01)
*H04L 29/06* (2006.01)
*H04W 12/00* (2009.01)

(52) U.S. Cl.
CPC ...... *H04L 61/2592* (2013.01); *H04L 67/2814* (2013.01); *H04L 67/2857* (2013.01); *H04L 67/2895* (2013.01); *H04W 8/005* (2013.01); *H04W 92/20* (2013.01); *H04L 63/164* (2013.01); *H04W 8/26* (2013.01); *H04W 12/001* (2019.01); *H04W 88/08* (2013.01)

(58) Field of Classification Search
CPC ............... H04L 61/2015; H04L 61/256; H04L 61/2592; H04L 29/08; H04L 67/2857; H04L 67/2814; H04L 67/2895
USPC .......................................................... 455/436
See application file for complete search history.

(56) References Cited

U.S. PATENT DOCUMENTS

| 2011/0222436 | A1* | 9/2011 | Zee ................. H04L 29/12547 370/254 |
| 2014/0026207 | A1* | 1/2014 | Wang ...................... H04L 41/28 726/12 |
| 2015/0109955 | A1 | 4/2015 | Wilkinson et al. |
| 2015/0289302 | A1* | 10/2015 | Xu ........................ H04W 76/10 370/329 |
| 2016/0212775 | A1 | 7/2016 | Xu et al. |
| 2016/0242147 | A1 | 8/2016 | Tarlazzi et al. |
| 2017/0188223 | A1* | 6/2017 | Gundavelli ............. H04W 8/04 |

OTHER PUBLICATIONS

International Searching Authority, "International Search Report and Written Opinion for PCT App. No. PCT/US2017/065891", "Foreign Counterpart to U.S. Appl. No. 15/839,656" dated Mar. 29, 2018, pp. 1-17, Published in: WO.

* cited by examiner

100

100

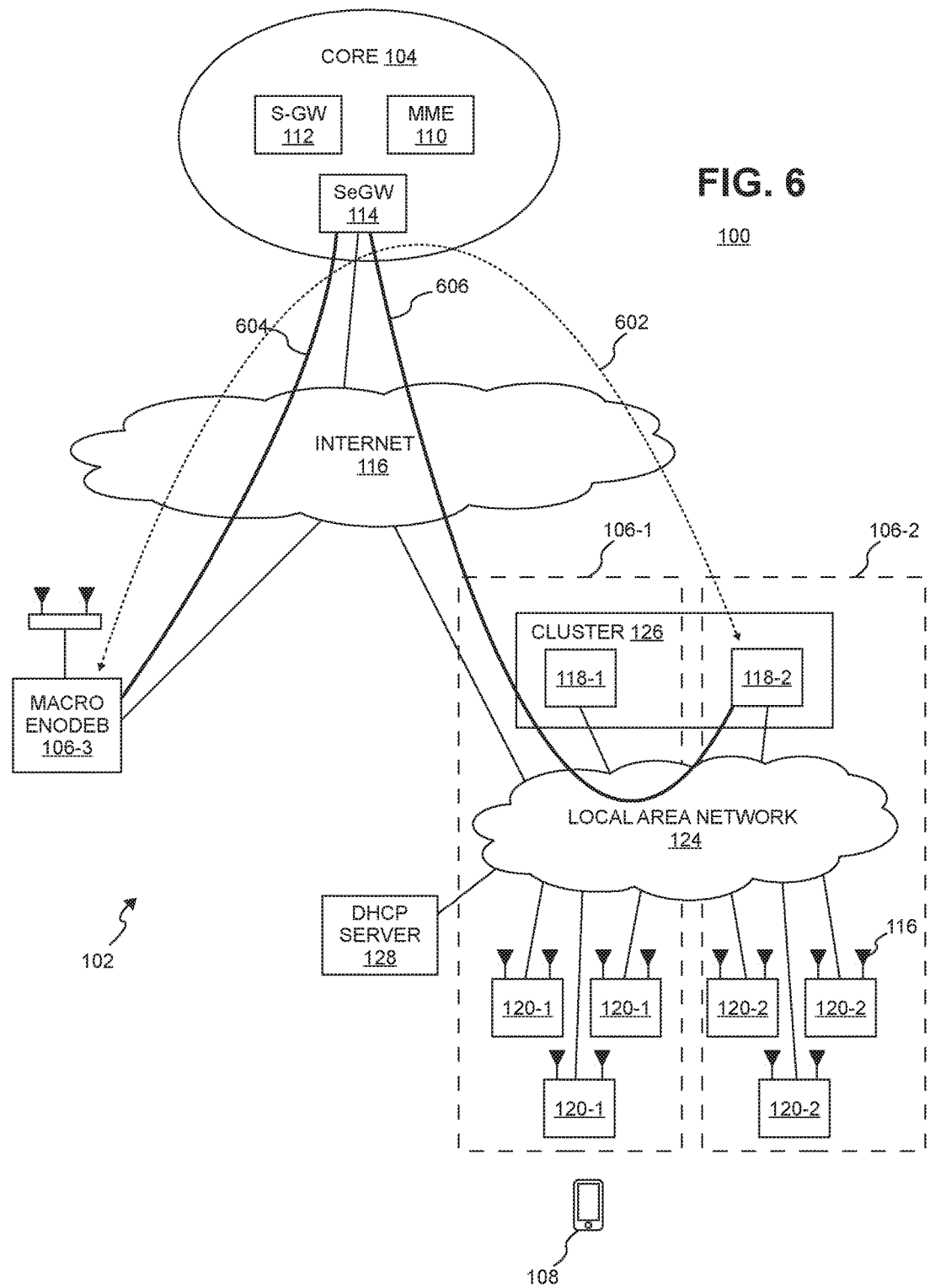

CLUSTER NEIGHBOR DISCOVERY IN CENTRALIZED RADIO ACCESS NETWORK USING TRANSPORT NETWORK LAYER (TNL) ADDRESS DISCOVERY

CROSS-REFERENCE TO RELATED APPLICATIONS

This application claims the benefit of U.S. Provisional Patent Application Ser. No. 62/433,013, titled "Cluster Neighbor Discovery In Centralized Radio Access Network Using Transport Network Layer (TNL) Address Discovery" and filed on Dec. 12, 2016, which is hereby incorporated herein by reference.

BACKGROUND

A Long Term Evolution (LTE) wireless network includes an Evolved Universal Terrestrial Radio Access Network (E-UTRAN) (also sometimes referred to simply as the "radio access network" or "RAN") and an Evolved Packet Core (EPC) network (also sometime referred to simply as the "core network").

The E-UTRAN comprises a set of base stations that wirelessly communicate with user equipment (such as smartphones) using licensed radio frequency spectrum. Each base station is also generally referred to as an "eNodeB" or "eNB."

One type of eNodeB is a "small cell" or "femtocell," which is a lower-power base station that is typically used to provide base station capacity within a home or enterprise (such as a business or public venue such as a hospital, arena, airport, shopping center, or the like). Such small cells or femtocells are also sometimes referred to as "Home eNodeBs" or "HeNBs."

Each eNB communicates with entities in the core network (such as, a Serving Gateway (S-GW) and a Mobility Management Entity (MME)) using the "51 interface" defined by the 3rd Generation Partnership Project (3GPP). Each eNB also communicates with other eNBs using the "X2 interface" defined by the 3GPP. These protocols are Internet Protocol (IP) based and often use public networks such as the Internet. As a result, traffic for the S1 and X2 interfaces is typically secured using one or more Internet Protocol Security (IPSec) tunnels.

A central security gateway (SeGW) function is typically implemented between an operator's core network and each eNB to secure communications between the core network and the eNB. The central SeGW function can be implemented as a separate physical entity or can be implemented as a part of another node.

In one configuration, both S1-interface traffic and X2-interface traffic for an eNodeB pass through the central security gateway. That is, even though the X2-interface traffic is communicated to another eNodeB and not to an entity in the core network, the X2-interface traffic is communicated back to the security gateway used for S1-interface traffic. This configuration is also referred to here as an "X2 Star" architecture. In the X2 Star architecture, IPSec Tunnel Mode (defined by the relevant IPSec standard) is used for X2-interface communications between two eNodeBs. A first IPSec tunnel is established between a first eNodeB and the central SeGW, and a second IPSec tunnel is established between a second eNodeB and the central SeGW. The central SeGW assigns a respective tunnel inner address (TIA) to the first and second eNodeBs, which are used as the transport network layer (TNL) addresses for communications that occur over the IPSec tunnels.

In another configuration, X2-interface traffic is not communicated back to the central security gateway used for S1-interface traffic but instead is communicated directly between the eNodeBs. This configuration is also referred to here as an "X2 Mesh" architecture. In the X2 Mesh architecture, IPSec Transport Mode (defined by the relevant IPSec standard) is used for X2-interface communications between two eNodeBs.

The 3GPP LTE technical specifications (specifically 3GPP TS 36.300) describe a procedure for TNL address discovery that can be used to determine a suitable TNL address for X2-interface communications. However, this TNL address discovery procedure does not support the X2 Mesh architecture, since it is configured to discover the central SeGW-assigned TIA address of a target eNodeB. The TIA address, by itself, is not sufficient to use IPSec Transport Mode for X2-interface communications with the X2 Mesh architecture.

SUMMARY

One embodiment is directed to a method comprising sending a request from a first base station to a second base station for a transport layer address assigned to the second base station that is suitable for establishing a base-station-to-base-station connection between the first base station and the second base station. The method further comprises determining, by the second base station, whether to include an outer address assigned to the second base station in a response to the request. In response to determining to include the outer address assigned to the second base station in the response, the response to the request to the first base station is sent, by the second base station. The response to the request includes a tunnel inner address assigned by a security gateway to the second base station and the outer address assigned to the second base station. The method further comprises determining, by the first base station, whether the outer address assigned to the second base station is included in the response, and, in response to determining that the outer address assigned to the second base station is included in the response, using the outer address assigned to the second base station to establish the base-station-to-base-station connection between the first base station and the second base station without using the security gateway.

Another embodiment is directed to a base station comprising an interface to communicatively couple said base station to a network. The base station is configured to perform at least some processing associated with implementing an air interface to provide wireless service. The base station is configured to respond to a request from a requesting base station for a transport layer address assigned to said base station that is suitable for establishing a base-station-to-base-station connection between the requesting base station and said base station by determining whether to include an outer address assigned to the second base station in a response to the request, and in response to determining to include the outer address assigned to said base station in the response, sending the response to the request to the requesting base station. The response to the request including a tunnel inner address assigned by a security gateway to said base station and the outer address assigned to said base station. The outer address assigned to said base station is used to establish the base-station-to-base-station connection between said base station and the requesting base station without using the security gateway.

Another embodiment is directed to a base station comprising an interface to communicatively couple said base station to a network. The base station is configured to perform at least some processing associated with implementing an air interface to provide wireless service. The base station is configured to: send a request to a replying base station for a transport layer address assigned to the replying base station that is suitable for establishing a base-station-to-base-station connection between said base station and the replying base station, receive a response to the request from the replying base station, and determine whether an outer address assigned to the replying base station is included in the response. In response to determining that the outer address assigned to the replying base station is included in the response, the outer address assigned to the replying base station is used to establish the base-station-to-base-station connection between said base station and the replying base station without using the security gateway.

Other embodiments are disclosed.

The details of various embodiments are set forth in the accompanying drawings and the description below. Other features and advantages will become apparent from the description, the drawings, and the claims.

DRAWINGS

FIGS. 4-6 show three examples of the operation of methods of FIGS. 2 and 3 in the system 100 of FIG. 1.

DETAILED DESCRIPTION

Figure 1:
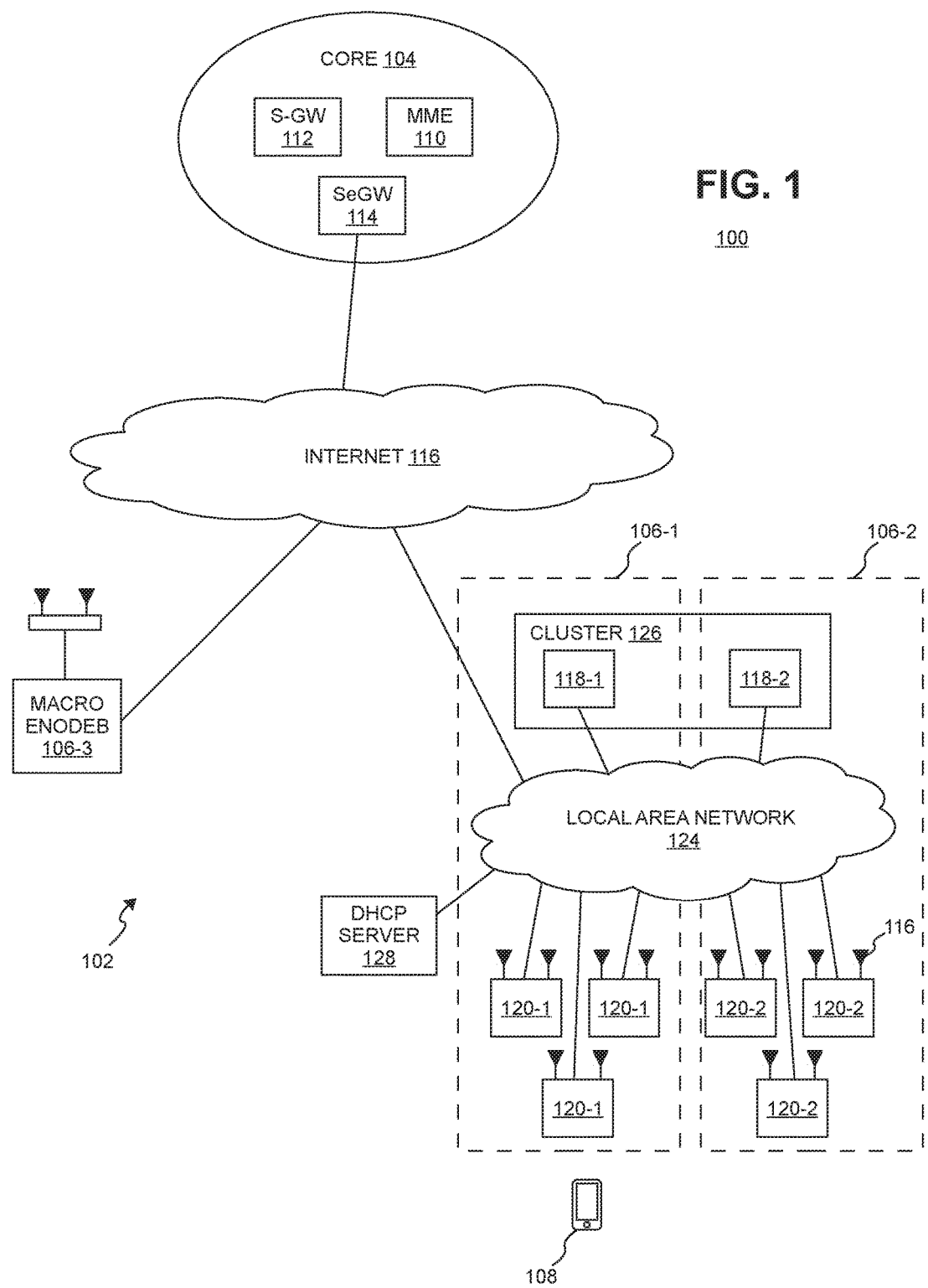
FIG. 1 is a block diagram of one exemplary embodiment of a wireless system in which the TNL address discovery techniques described here can be used.

FIG. 1 is a block diagram of one exemplary embodiment of a wireless system 100 in which the TNL address discovery techniques described here can be used.

In the exemplary embodiment shown in FIG. 1, the wireless system 100 comprises a radio access network (RAN) 102 and a core network 104. In this exemplary embodiment, the RAN 102 is described here as being implemented as a Long Term Evolution (LTE) radio access network providing wireless service using an LTE air interface. LTE is a standard developed by the 3GPP standards organization.

In this embodiment, the RAN 102 comprises a plurality of base stations 106 (also referred to here as "LTE Evolved Node Bs," "eNodeBs," or "eNBs") that are used to provide user equipment 108 with mobile access to the wireless network operator's core network 104 in order to enable the user equipment 108 to wirelessly communicate data and voice (using, for example, Voice over LTE (VoLTE) technology).

Also, in this exemplary LTE embodiment, the core network 104 is implemented as an Evolved Packet Core (EPC) comprising standard LTE EPC network elements such as, for example, a mobility management entity (MME) 110, a Serving Gateway (S-GW) 112 and, a Security Gateway (SeGW) 114.

In the exemplary embodiment shown in FIG. 1, the Internet 116 is used for back-haul between the RAN 100 and the core network 104.

Moreover, in this exemplary embodiment, each base station 106 communicates with the MME 110 and S-GW 112 in the EPC core network 104 using the LTE S1 interface and communicates with other base stations 106 using the LTE X2 interface.

Each base station 106 can be implemented using one or more nodes that implement the various base-station functions necessary to implement the LTE air-interface and to interact with the core network 104. The one or more nodes that implement each base station 106 are referred to collectively as a "base station 106" or "eNodeB 106" for ease of explanation.

Each base station 106 includes or is coupled to one or more antennas 116 via which downstream radio frequency signals are radiated to user equipment 108 and via which upstream radio frequency signals transmitted by user equipment 108 are received.

In the example showing FIG. 1, three base stations 106 are shown and individually referenced use reference numerals 106-1, 106-2, and 106-3, respectively.

In this example, the first two base stations 106-1 and 106-2 are each implemented using multiple nodes in a point-to-multipoint distributed base station architecture. For each of these base stations 106-1 and 106-2, a portion of the base station functions are implemented by a respective central unit (also referred to as a "controller") 118-1 and 118-2 and by respective multiple remote units (also referred to here as "radio points") 120-1 and 120-2 that are located remotely from the respective controller 118-1 and 118-2. Each radio point 120-1 and 120-2 includes or is coupled to one or more antennas 122 via which downstream radio frequency signals are radiated to user equipment 108 and via which upstream radio frequency signals transmitted by user equipment 108 are received. In this example, each controller 118-1 and 118-2 is communicatively coupled to its respective radio points 120-1 and 120-2 using a common Ethernet local area network 124. Details regarding such an architecture can be found in U.S. patent application Ser. No. 13/762,283, filed on Feb. 7, 2013, and titled "RADIO ACCESS NETWORKS," which is hereby incorporated herein by reference.

In the example shown in FIG. 1, the controllers 118-2 and 118-2 and radio points 120-1 and 120-2 are configured to implement a Centralized RAN (C-RAN), where the controllers 118-1 and 118-2 are co-located together. In the example shown in FIG. 1, the co-located controllers 118-1 and 118-2 are described here as being in the same cluster 126. This C-RAN can be deployed to provide base station capacity within an enterprise such as a business or public venue such as a hospital, arena, airport, shopping center, or the like.

In the example shown in FIG. 1, the third base station 106-3 is implemented as a macro base station.

It is to be understood, however, that each base station 106 can be implemented in other ways (for example, as a traditional monolithic macro or small cell base station).

In the exemplary embodiment, the back-haul between the base stations 106 and the core network 104 is implemented using one or more IP networks (including, in this example, the local area network 124 and the Internet 116). At least one Dynamic Host Configuration Protocol (DHCP) server 120 is coupled to the local area network 124 and that assigns IP addresses to the base stations 106-1 and 106-2 that are also coupled to the local area network 124. These IP addresses are also referred to here as "outer" IP addresses.

In the example shown in FIG. 1, the LTE X2 interface established between some of the eNodeBs 106 (eNodeBs 106-1 and 106-2 in FIG. 1) is established using the X2 Mesh architecture described above. As noted above, in the X2 Mesh architecture, IPSec Transport Mode is used for X2-interface communications between the two eNodeBs 106-1 and 106-2.

Also, in this example, the LTE X2 interface established between some of the eNodeBs 106 (eNodeBs 106-1 and 106-3 in FIG. 1) is established using the X2 Star architecture described above. As noted above, in the X2 Star architecture, IPSec Tunnel Mode is used for X2-interface communications between the two eNodeBs 106-1 and 106-3.

In this example, the first and second eNodeBs 106-1 and 106-2 are configured to use an extended version of the TNL address discovery procedure, the standard version of which is defined in 3GPP Technical Specification 36.413. This extended version of the TNL address discovery procedure has been extended to support the X2 Mesh architecture. Also, in this example, the third eNodeB 106-3 does not use the extended version of the TNL address discovery procedure and, instead, uses the standard (non-extended) version of the TNL address discovery procedure.

Figure 2:
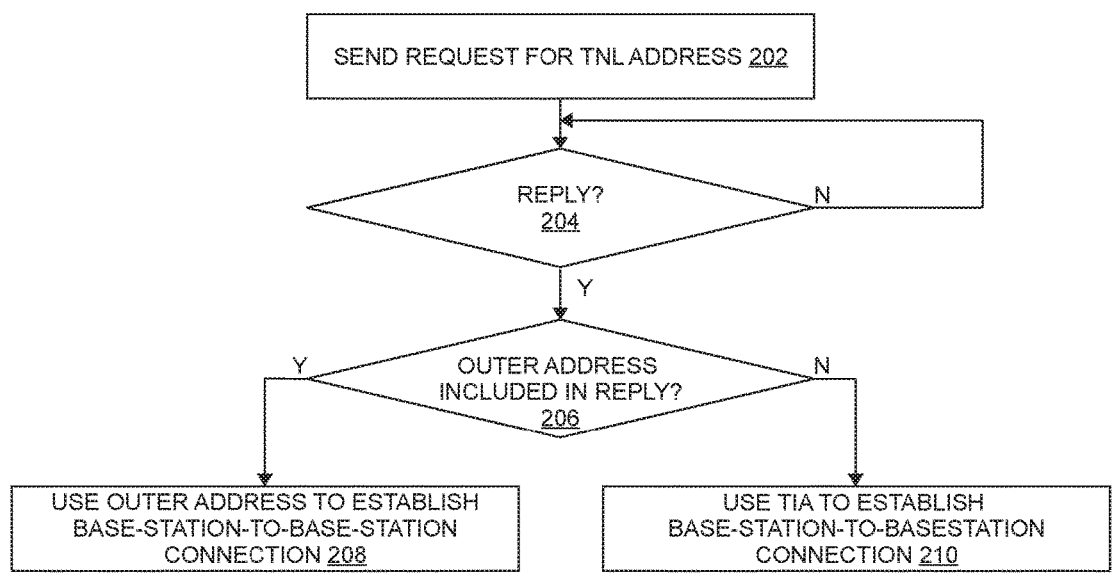
FIG. 2 is a flow diagram of an exemplary embodiment of a method of discovering the transport layer address for an LTE X2 interface or other base-station-to-base-station connection.

FIG. 2 is a flow diagram of an exemplary embodiment of a method 200 of discovering the transport layer address for an LTE X2 interface or other base-station-to-base-station connection.

The exemplary embodiment of method 200 shown in FIG. 2 is described here as being implemented using the system 100 shown in FIG. 1. It is to be understood that other embodiments can be implemented in other ways.

The blocks of the flow diagrams shown in FIG. 2 have been arranged in a generally sequential manner for ease of explanation; however, it is to be understood that this arrangement is merely exemplary, and it should be recognized that the processing associated with method 200 (and the blocks shown in FIG. 2) can occur in a different order (for example, where at least some of the processing associated with the blocks is performed in parallel and/or in an event-driven manner).

Method 200 can be performed when one eNodeB (referred to here as the "requesting" eNodeB) detects a new eNodeB (referred to here as the "replying" eNodeB). The processing associated with FIG. 2 is performed by the requesting eNodeB.

Method 200 is performed by a requesting eNodeB that implements the extended version of the TNL address discovery procedure described here. Method 200 is used by the requesting eNodeB to send a request to a replying eNodeB for a transport layer address assigned to the replying eNodeB that is suitable for establishing a base-station-to-base-station connection between the requesting eNodeB and the replying eNodeB. In this example, the base-station-to-base-station connection is an LTE X2 interface implemented over one or more IPSec connections, and the transport layer address is an Internet Protocol (IP) address.

Method 200 can be used by the requesting eNodeB to request a transport layer address from a replying eNodeB that either implements the extended version of the TNL address discovery procedure described here or that implements the standard (non-extended) TNL address discovery procedure.

In general, the requesting eNodeB can detect a new eNodeB (the replying eNodeB) using the LTE Automatic Neighbor Relation (ANR) function. The LTE ANR function provides the requesting eNodeB with the eNodeB identifier for the replying eNodeB. However, the LTE ANR function does not provide a suitable TNL address to establish an X2 interface with the replying eNodeB. Method 200 can be performed by the requesting eNodeB in order to discover such a TNL address for the new replying eNodeB.

At block 202, the requesting eNodeB sends a request to the replying eNodeB for a transport layer address assigned to the replying eNodeB that is suitable for establishing a base-station-to-base-station connection between the requesting eNodeB and that replying eNodeB. As noted above, in this example, the base-station-to-base-station connection is an LTE X2 interface implemented using one or more IPSec connections, and the transport layer address is an Internet Protocol (IP) address.

In this example, the requesting eNodeB sends the TNL address request by sending an eNB CONFIGURATION TRANSFER message to the MME 110. The eNB CONFIGURATION TRANSFER message includes a request for the TNL address of the replying eNodeB. More specifically, the eNB CONFIGURATION TRANSFER message includes a Self Optimizing Network (SON) Information Request Information Element (IE) requesting the TNL address of the replying eNodeB. The source of the eNB CONFIGURATION TRANSFER message is the eNodeB identifier for the requesting eNodeB, and the target of the eNB CONFIGURATION TRANSFER message is the eNodeB identifier for the replying eNodeB.

The MME 110 receives the eNB CONFIGURATION TRANSFER message and relays the TNL address request to the replying eNodeB. The MME 110 does this by sending an MME CONFIGURATION TRANSFER message to the replying eNodeB that includes the SON Information Request IE requesting the TNL address of the replying eNodeB. The MME 110 identifies the replying eNodeB using the eNodeB identifier for the replying eNodeB included in the eNB CONFIGURATION TRANSFER message received from the requesting eNodeB. The source of the MME CONFIGURATION TRANSFER message is the eNodeB identifier for the requesting eNodeB, and the target of the MME CONFIGURATION TRANSFER message is the eNodeB identifier for the replying eNodeB.

The replying eNodeB receives the MME CONFIGURATION TRANSFER message that includes the SON Information Request IE requesting the TNL address of the replying eNodeB. In response to this message, the replying eNodeB sends a reply to the TNL address request. The reply can be either a "standard" reply that includes only the TIA address assigned to the replying eNodeB or an "extended" reply that includes both the TIA address and the outer address assigned to the replying eNodeB.

The TIA address can be the IP address assigned by the security gateway 114 to the replying eNodeB in connection with the S1 interface that is established for that eNodeB.

When the requesting eNodeB receives a reply to the TNL address request (block 204), the requesting eNodeB determines whether an outer address assigned to the replying eNodeB is included in the TNL address reply (block 206). That is, the requesting eNodeB determines whether the received reply is a "standard" reply that includes only the TIA address assigned to the replying eNodeB (sent from a replying eNodeB that implements the standard (non-extended) TNL address discovery procedure) or an "extended" reply that includes both the TIA address and the outer address assigned to the replying eNodeB (sent from a replying eNodeB that implements the extended version of the TNL address discovery procedure described here).

In the example implemented in the system 100 of FIG. 1, the outer address is an IP address assigned to the replying eNodeB by the DHCP sever 128 and that the replying eNodeB uses for communicating over the local area network 124.

In this example, the reply will be in the form of a MME CONFIGURATION TRANSFER message that includes a SON Information Reply IE. The SON Information Reply IE includes the reply originally sent from the replying eNodeB. The source of the MME CONFIGURATION TRANSFER message is the eNodeB identifier for the replying eNodeB, and the target of the MME CONFIGURATION TRANSFER message is the eNodeB identifier for the requesting eNodeB.

The requesting eNodeB can determine whether an outer address assigned to the replying eNodeB is included in the TNL address reply in many ways. For example, the requesting eNodeB can do this by checking the reply itself to see if it is an "extended" reply that includes both the TIA address and the outer address assigned to the replying eNodeB or a "standard" reply that includes only the TIA address assigned to the replying eNodeB.

Alternatively, the requesting eNodeB can check the eNodeB identifier for the replying eNodeB to see if the replying eNodeB is communicatively coupled to the same local area network 124 such that those two eNodeBs are able to communicate with each other using only local communications that are communicated over the local area network 124. For example, as shown in FIG. 1, eNodeBs 106-1 and 106-2 (which are implemented using a distributed, point-to-multipoint architecture) are coupled to the same local area network 124 and are able to communicate directly with each other using only local communications communicated over the local area network 124. The requesting eNodeB can make this determination prior to or after receiving the reply to the TNL address request. The requesting eNodeB can be manually supplied with the eNodeB identifiers of those eNodeBs that are coupled to the same local area network 124 as the requesting eNodeB. The requesting eNodeB can discover or be provided with the eNodeB identifiers of those eNodeBs that are coupled to the same local area network 124 as the requesting eNodeB in other ways.

If it is the case that the TNL address reply includes an outer address assigned to the replying eNodeB, the requesting eNodeB uses the outer address assigned to the replying eNodeB to establish the base-station-to-base-station connection between the requesting eNodeB and the replying eNodeB without using the security gateway 114 (block 208). In the example implemented in the system 100 of FIG. 1, in this situation, the requesting eNodeB uses the outer IP address assigned to the replying eNodeB by the DHCP sever 128 in order to establish an X2 interface between the requesting eNodeB and the replying eNodeB by establishing an IPSec connection directly between the requesting eNodeB and the replying eNodeB using the X2 Mesh architecture described above. IPSec Transport Mode is used for the IPSec connection.

If the requesting eNodeB determines that an outer address assigned to the replying eNodeB is not included in the TNL address reply, the requesting eNodeB uses the TIA address assigned to the replying eNodeB 106 to establish the base-station-to-base-station connection between the requesting eNodeB and the replying eNodeB using the security gateway 114 (block 210). In the example implemented in the system 100 of FIG. 1, in this situation, the requesting eNodeB uses the TIA IP address assigned to the replying eNodeB by the SeGW 114 in order to establish an X2 interface between the requesting eNodeB and the replying eNodeB using the X2 Star architecture described above. A first IPSec connection is established between the requesting eNodeB and the SeGW 114, and a second IPSec connection is established between the replying eNodeB and the SeGW 114. IPSec Tunnel Mode is used for, and an IPSec tunnel is established over, the IPSec connections.

Figure 3:
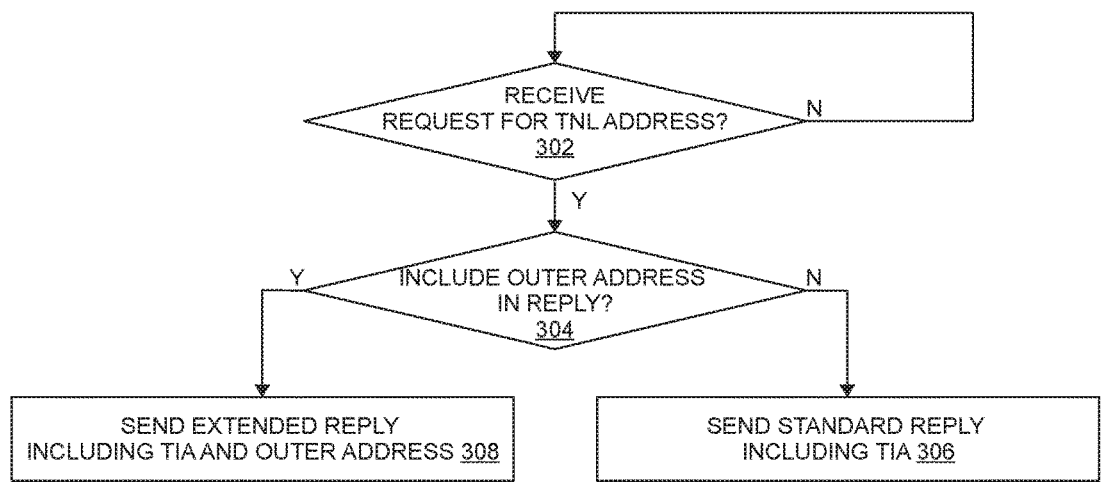
FIG. 3 is a flow diagram of an exemplary embodiment of a method of discovering the transport layer address for an LTE X2 interface or other base-station-to-base-station connection.

FIG. 3 is a flow diagram of an exemplary embodiment of a method 300 of discovering the transport layer address for an LTE X2 interface or other base-station-to-base-station connection.

The exemplary embodiment of method 300 shown in FIG. 3 is described here as being implemented using the system 100 shown in FIG. 1.

The blocks of the flow diagrams shown in FIG. 3 have been arranged in a generally sequential manner for ease of explanation; however, it is to be understood that this arrangement is merely exemplary, and it should be recognized that the processing associated with method 300 (and the blocks shown in FIG. 3) can occur in a different order (for example, where at least some of the processing associated with the blocks is performed in parallel and/or in an event-driven manner).

Method 300 can be performed when one eNodeB (referred to here as the "requesting" eNodeB) detects a new eNodeB (referred to here as the "replying" eNodeB). The processing associated with FIG. 3 is performed by the replying eNodeB.

Method 300 is performed by a replying eNodeB that implements the extended version of the TNL address discovery procedure described here. Method 300 can be used by the replying eNodeB to reply to a request for a transport layer address that was sent from a requesting eNodeB that either implements the extended version of the TNL address discovery procedure described here or that implements the standard (non-extended) TNL address discovery procedure.

At block 302, the replying eNodeB receives a TNL address request from a requesting eNodeB.

As noted above in connection with FIG. 2, the replying eNodeB will receive an MME CONFIGURATION TRANSFER message that includes a SON Information Request Information Element containing the TNL address of the replying eNodeB that was sent from the requesting eNodeB.

In response, the replying eNodeB determines whether to include an outer address assigned to it in a reply to the TNL address request (block 304). That is, the requesting eNodeB determines whether the received reply is a "standard" reply that includes only the TIA address assigned to the replying eNodeB (sent from a replying eNodeB 106 that implements the standard (non-extended) TNL address discovery procedure) or an "extended" reply that includes both the TIA address and the outer address assigned to the replying eNodeB (sent from a replying eNodeB that implements the extended version of the TNL address discovery procedure described here).

The replying eNodeB can make this determination by checking the eNodeB identifier for the requesting eNodeB to see if the requesting eNodeB is communicatively coupled to the same local area network 124 such that those two eNodeBs are able to communicate with each other using only local communications that are communicated over the local area network 124. For example, as shown in FIG. 1, eNodeBs 106-1 and 106-2 (which are implemented using a distributed, point-to-multipoint architecture) are coupled to the same local area network 124 and are able to communicate directly with each other using only local communications communicated over the local area network 124. The replying eNodeB can be manually supplied with the eNodeB identifiers of those eNodeBs that are coupled to the same local area network 124 as the replying eNodeB. The replying eNodeB can discover or be provided with the eNodeB identifiers of those eNodeBs that are coupled to the same local area network 124 as the requesting eNodeB in other ways.

If the replying eNodeB determines that it should not include the outer address assigned to it in the reply to the TNL address request, the replying eNodeB sends a "standard" reply to the TNL address request that includes only the tunnel inner address (TIA) IP address assigned to it by the SeGW 114 (block 306). The reply is sent to the requesting eNodeB.

If the replying eNodeB determines that it should include the outer address assigned to it in the reply to the TNL address request, the replying eNodeB sends an "extended" reply to the TNL address request that includes both the TIA IP address assigned to the replying eNodeB by the SeGW 114 and the outer IP address assigned to the replying eNodeB by the DHCP server 120 (block 308).

In either case, the replying eNodeB sends an eNB CONFIGURATION TRANSFER message to the MME 110 that includes a SON Information Reply Information Element that includes the reply—either a standard reply containing only the TIA IP address assigned to the replying eNodeB by the SeGW 114 or an extended reply containing both the TIA IP address assigned to the replying eNodeB by the SeGW 114 and the outer IP address assigned to the replying eNodeB by the DHCP server 128. The source of the eNB CONFIGURATION TRANSFER message is the eNodeB identifier for the replying eNodeB, and the target of the eNB CONFIGURATION TRANSFER message is the eNodeB identifier for the requesting eNodeB.

The MME 110 receives the eNB CONFIGURATION TRANSFER message sent from the replying eNodeB and relays the TNL address reply to the requesting eNodeB. The MME 110 does this by sending an MME CONFIGURATION TRANSFER message to the requesting eNodeB that includes the SON Information Reply IE containing the reply to the TNL address request. The MME 110 identifies the requesting eNodeB using the eNodeB identifier for the requesting eNodeB included in the eNB CONFIGURATION TRANSFER message received from the replying eNodeB. The source of the MME CONFIGURATION TRANSFER message is the eNodeB identifier for the replying eNodeB, and the target of the MME CONFIGURATION TRANSFER message is the eNodeB identifier for the requesting eNodeB.

The requesting eNodeB receives the MME CONFIGURATION TRANSFER message that includes the SON Information Reply IE including the TNL address of the replying eNodeB. In response to this message, the requesting eNodeB uses the TNL address to establish an LTE X2 interface between the requesting eNodeB 106 and the replying eNodeB 106 and associated IPSec connections.

Figure 4:
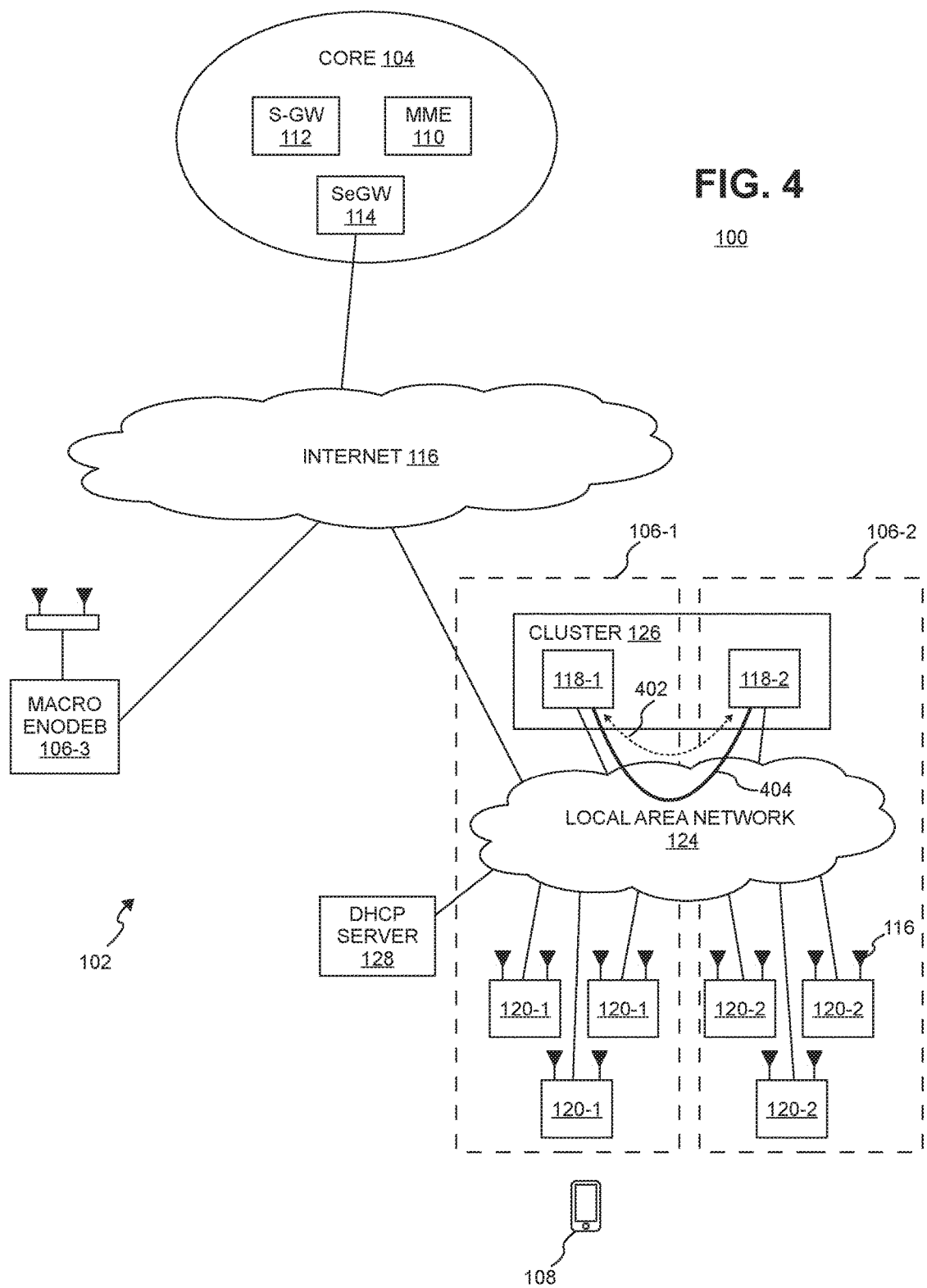
Figure 5:
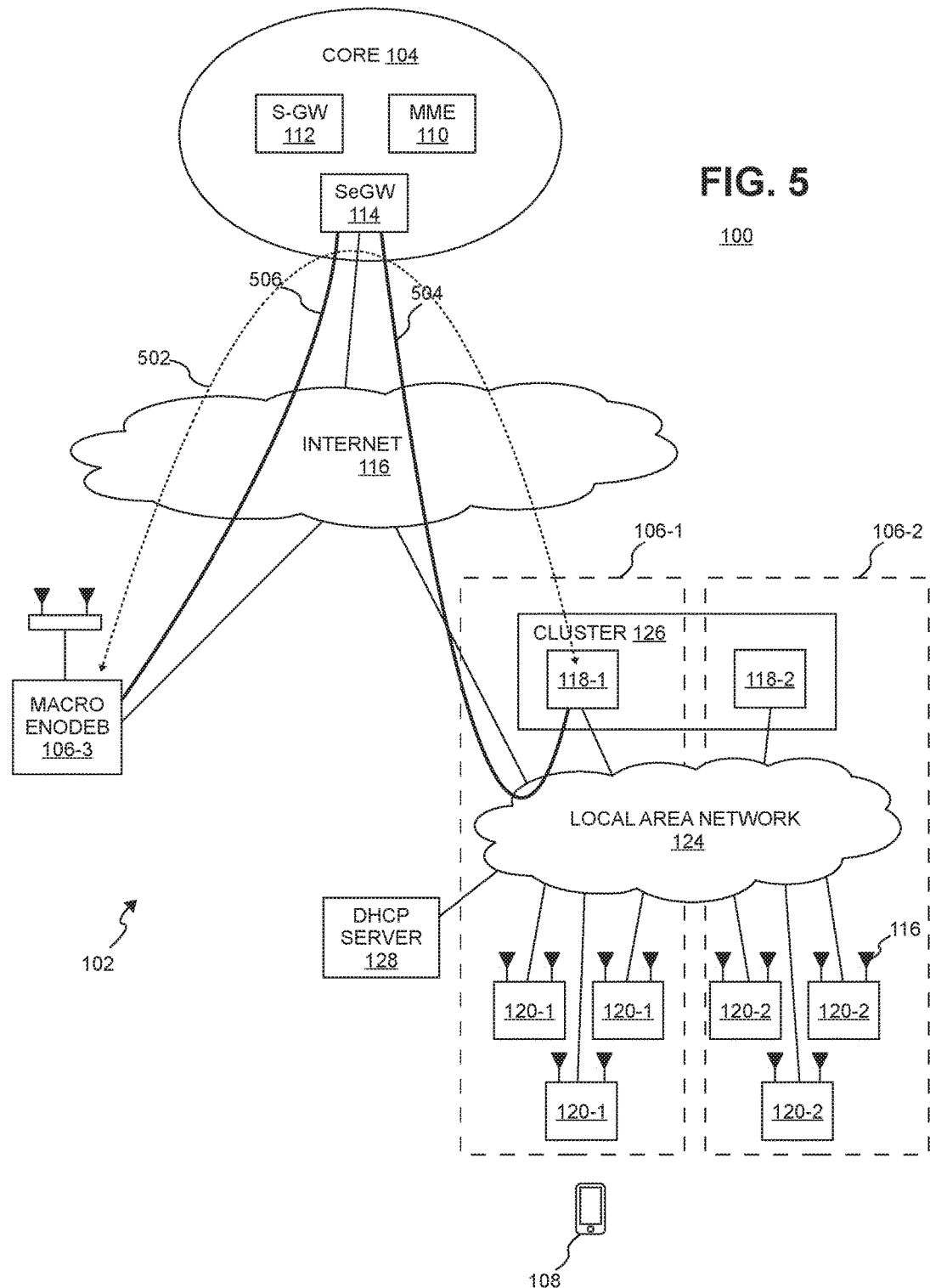

FIGS. 4-6 show three examples of the operation of methods 200 and 300 above in the system 100 of FIG. 1.

In the example shown in FIG. 4, the requesting eNodeB is the first eNodeB 106-1 described above in connection with FIG. 1, and the replying eNodeB is the second eNodeB 106-2 described above in connection with FIG. 1. In this example, the first and second eNodeBs 106-1 and 106-2 both implement the extended version of the TNL address discovery procedure described above.

The first eNodeB 106-1 (the requesting eNodeB) sends a request to the second eNodeB 106-2 (the replying eNodeB) for a transport layer address assigned to the second eNodeB 106-2 that is suitable for establishing a base-station-to-base-station connection between those eNodeB 106-1 and 106-2.

The second eNodeB 106-2 receives the TNL address request from the first eNodeB 106-1 and, in response to receiving that request, the second eNodeB 106-2 checks if the source of the TNL address request is an eNodeB that is in the same cluster 126 as the second eNodeB 106-2.

Each controller 118 in the cluster 126 can be manually supplied with the eNodeB identifiers for the other controllers 118 in that cluster 126. Each controller 118 in the cluster 126 can obtain or determine the eNodeB identifiers for the other controllers 118 in that cluster 126 in other ways. Each controller 118 in the cluster 126 can then check if the eNodeB identifier in the request matches one of the eNodeB identifiers for the controllers 118 in that cluster 126.

The controller 118-1 for the first eNodeB 106-1 and the controller 118-2 for the second eNodeB 106-2 are part of the same cluster 126 and are both connected to the same local area network 124 (indeed, in many cases, they will be co-located in the same rack). As a result, the second eNodeB 106-2 sends an "extended" reply to the TNL address request that includes both the TIA IP address assigned to the second eNodeB 106-2 by the SeGW 114 and the outer IP address assigned to the second eNodeB 106-2 by the DHCP server 128.

The first eNodeB 106-1 receives the reply from the second eNodeB 106-2 and determines whether an outer address assigned to the second eNodeB 106-2 is included in the reply. The first eNodeB 106-1 does this by checking if the source of the reply is an eNodeB that is in the same cluster 126 as the first eNodeB 106-1, which it is in this example.

As a result, the first eNodeB 106-1 uses the outer IP address assigned to the second eNodeB 106-2 by the DHCP sever 120 in order to establish an X2 interface 402 between the first eNodeB 106-1 and the second eNodeB 106-2 by establishing an IPSec connection 404 directly between the first eNodeB 106-1 and the second eNodeB 106-2 using the X2 Mesh architecture described above. IPSec Transport Mode is used for the IPSec connection 404.

In the example shown in FIG. 5, the requesting eNodeB is the first eNodeB 106-1 described above in connection with FIG. 1, and the replying eNodeB is the third eNodeB 106-3 described above in connection with FIG. 1. As noted above, in this example, the first eNodeB 106-1 implements the extended version of the TNL address discovery procedure described above but the third eNodeB 106-3 does not and instead implements the standard version of the TNL address discovery procedure.

The first eNodeB 106-1 (the requesting eNodeB) sends a request to the third eNodeB 106-3 (the replying eNodeB) for a transport layer address assigned to the third eNodeB 106-3 that is suitable for establishing a base-station-to-base-station connection between those eNodeB 106-1 and 106-3.

The third eNodeB 106-3 receives the TNL address request from the first eNodeB 106-1. In this example, the third eNodeB 106-3 implements the standard version of the TNL address discovery procedure and, as a result, the third eNodeB 106-3 sends a "standard" reply to the TNL address request that includes only the tunnel inner address (TIA) IP address assigned to it by the SeGW 114.

The first eNodeB 106-1 receives the reply from the third eNodeB 106-3 and determines whether an outer address assigned to the third eNodeB 106-3 is included in the reply.

The first eNodeB 106-1 does this by checking if the source of the reply is an eNodeB that is in the same cluster 126 as the first eNodeB 106-1, which it is not in this example.

As a result, the first eNodeB 106-1 uses the TIA IP address assigned to the third eNodeB 106-3 by the SeGW 114 in order to establish an X2 interface 502 between the first eNodeB 106-1 and the third eNodeB 106-3 using the X2 Star architecture described above. A first IPSec connection 504 is established between the first eNodeB 106-1 and the SeGW 114, and a second IPSec connection 506 is established between the third eNodeB 106-3 and the SeGW 114. IPSec Tunnel Mode is used for, and an IPSec tunnel is established over, the IPSec connections 504 and 506.

In the example shown in FIG. 6, the requesting is the third eNodeB 106-1 described above in connection with FIG. 1, and the replying eNodeB is the second eNodeB 106-2 described above in connection with FIG. 1. As noted above, in this example, the second eNodeB 106-1 implements the extended version of the TNL address discovery procedure described above but the third eNodeB 106-3 does not and instead implements the standard version of the TNL address discovery procedure.

The third eNodeB 106-3 (the requesting eNodeB in this example) sends a request to the second eNodeB 106-2 (the replying eNodeB in this example) for a transport layer address assigned to the second eNodeB 106-2 that is suitable for establishing a base-station-to-base-station connection between those eNodeB 106-3 and 106-2.

The second eNodeB 106-2 receives the TNL address request from the third eNodeB 106-3. In this example, the second eNodeB 106-2 implements the extended version of the TNL address discovery procedure and, as a result, in response to receiving that TNL address request, the second eNodeB 106-2 checks if the source of the TNL address request is an eNodeB that is in the same cluster 126 as the second eNodeB 106-2, which is not the case in this example.

As a result, the second eNodeB 106-2 sends, to the third eNodeB 106-3, a "standard" reply to the TNL address request that includes only the tunnel inner address (TIA) IP address assigned to it by the SeGW 114.

The third eNodeB 106-3 receives the reply from the second eNodeB 106-2 and uses the TIA IP address assigned to the second eNodeB 106-2 by the SeGW 114 in order to establish an X2 interface 602 between the third eNodeB 106-3 and the second eNodeB 106-2 using the X2 Star architecture described above. A first IPSec connection 604 is established between the third eNodeB 106-3 and the SeGW 114, and a second IPSec connection 606 is established between the second eNodeB 106-2 and the SeGW 114. IPSec Tunnel Mode is used for, and an IPSec tunnel is established over, the IPSec connections 604 and 606.

By using the extended version of the TNL address discovery procedure defined in 3GPP Technical Specification 36.413, a TNL address suitable for establishing an LTE X2 interface connection using the X2 Mesh architecture can be automatically discovered. The extended version of the TNL address discovery procedure is backwards compatible with eNodeBs 106 that do not support the extend version of the TNL address discovery procedure. Also, the MME 110 does not need to be changed in order to support the extended version of the TNL address discovery procedure.

The methods and techniques described here may be implemented in digital electronic circuitry, or with a programmable processor (for example, a special-purpose processor or a general-purpose processor such as a computer) firmware, software, or in combinations of them. Apparatus embodying these techniques may include appropriate input and output devices, a programmable processor, and a storage medium tangibly embodying program instructions for execution by the programmable processor. A process embodying these techniques may be performed by a programmable processor executing a program of instructions to perform desired functions by operating on input data and generating appropriate output. The techniques may advantageously be implemented in one or more programs that are executable on a programmable system including at least one programmable processor coupled to receive data and instructions from, and to transmit data and instructions to, a data storage system, at least one input device, and at least one output device. Generally, a processor will receive instructions and data from a read-only memory and/or a random access memory. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and DVD disks. Any of the foregoing may be supplemented by, or incorporated in, specially-designed application-specific integrated circuits (ASICs).

A number of embodiments of the invention defined by the following claims have been described. Nevertheless, it will be understood that various modifications to the described embodiments may be made without departing from the spirit and scope of the claimed invention. Accordingly, other embodiments are within the scope of the following claims.

Example Embodiments

Example 1 includes a method comprising: sending a request from a first base station to a second base station for a transport layer address assigned to the second base station that is suitable for establishing a base-station-to-base-station connection between the first base station and the second base station; determining, by the second base station, whether to include an outer address assigned to the second base station in a response to the request; in response to determining to include the outer address assigned to the second base station in the response, sending, by the second base station, the response to the request to the first base station, the response to the request including a tunnel inner address assigned by a security gateway to the second base station and the outer address assigned to the second base station; determining, by the first base station, whether the outer address assigned to the second base station is included in the response; and in response to determining that the outer address assigned to the second base station is included in the response, using the outer address assigned to the second base station to establish the base-station-to-base-station connection between the first base station and the second base station without using the security gateway.

Example 2 includes the method of Example 1, wherein the base-station-to-base-station connection is used to implement an LTE X2 interface between the first base station and the second base station.

Example 3 includes the method of Example 2, wherein the outer address assigned to the second base station comprises an Internet Protocol (IP) address assigned by a Dynamic Host Configuration Protocol (DHCP) server; and wherein using the outer address assigned to the second base station to establish the base-station-to-base-station connection between the first base station and the second base station without using the security gateway comprises: using the IP address assigned to the second base station by the DHCP server to establish the LTE X2 interface between the first base station and the second base station using an X2 mesh architecture that comprises an Internet Protocol Security (IPSec) connection between the first base station and the second base station without using the security gateway.

Example 4 includes the method of any of the Examples 1-3, further comprising: in response to the second base station determining not to include the outer address assigned to the second base station in the response, sending, by the second base station, the response to the request to the first base station, the response to the request including the tunnel inner address assigned by the security gateway to the second base station; and in response to the first base station determining that the outer address assigned to the second base station is not included in the response, using the tunnel inner address assigned to the second base station to establish the base-station-to-base-station connection between the first base station and the second base station using the security gateway.

Example 5 includes the method of Example 4, wherein the base-station-to-base-station connection is used to implement an LTE X2 interface between the first base station and the second base station; wherein the tunnel inner address assigned to the second base station comprises an Internet Protocol (IP) address assigned by the security gateway; and wherein using the tunnel inner address assigned to the second base station to establish the base-station-to-base-station connection between the first base station and the second base station using the security gateway comprises: using the IP address assigned to the second base station by the security gateway to establish the LTE X2 interface between the first base station and the second base station using an X2 Star architecture that comprises a first Internet Protocol Security (IPSec) connection established between the first base station and the security gateway and a second IPSec connection established between the security gateway and the second base station.

Example 6 includes the method of any of the Example 1-5, wherein the first base station comprises a first controller and at least one first radio point located remotely from the first controller; and wherein the second base station comprises a second controller and at least one second radio point located remotely from the second controller.

Example 7 includes the method of any of the Examples 1-6, wherein determining, by the second base station, whether to include the outer address assigned to the second base station in the response to the request comprises: determining, by the second base station, whether the first base station and the second base station are in the same cluster.

Example 8 includes the method of any of the Examples 1-7, wherein determining, by the first base station, whether the outer address assigned to the second base station is included in the response comprises: determining, by the second base station, whether the first base station and the second base station are in the same cluster.

Example 9 includes the method of any of the Examples 1-8, wherein the network comprises an ETHERNET network.

Example 10 includes the method of any of the Examples 1-9, wherein the first base station and the second base station are a part of a centralized radio access network (C-RAN).

Example 11 includes the method of any of the Examples 1-10, wherein determining, by the second base station, whether to include the outer address assigned to the second base station in the response to the request comprises: checking whether the first base station and the second base station are able to communicate with each other using only local communications.

Example 12 includes the method of any of the Examples claim 1-11, wherein determining, by the first base station, whether the outer address assigned to the second base station is included in the response comprises: checking whether the first base station and the second base station are able to communicate with each other using only local communications.

Example 13 includes the method of any of the Examples 1-12, wherein determining, by the first base station, whether the outer address assigned to the second base station is included in the response comprises: checking the response to determine if the outer address assigned to the second base station is included in the response.

Example 14 includes a base station comprising: an interface to communicatively couple said base station to a network; wherein said base station is configured to perform at least some processing associated with implementing an air interface to provide wireless service; wherein said base station is configured to respond to a request from a requesting base station for a transport layer address assigned to said base station that is suitable for establishing a base-station-to-base-station connection between the requesting base station and said base station by: determining whether to include an outer address assigned to the second base station in a response to the request; in response to determining to include the outer address assigned to said base station in the response, sending the response to the request to the requesting base station, the response to the request including a tunnel inner address assigned by a security gateway to said base station and the outer address assigned to said base station; and wherein the outer address assigned to said base station is used to establish the base-station-to-base-station connection between said base station and the requesting base station without using the security gateway.

Example 15 includes the base station of Example 14, wherein the base-station-to-base-station connection is used to implement an LTE X2 interface between said base station and the requesting base station.

Example 16 includes the base station of Example 15, wherein the outer address assigned to said base station comprises an Internet Protocol (IP) address assigned by a Dynamic Host Configuration Protocol (DHCP) server; and wherein the IP address assigned to said base station by the DHCP server is used to establish the LTE X2 interface between the requesting base station and said base station using an X2 mesh architecture that comprises an Internet Protocol Security (IPSec) connection between the requesting base station and said base station without using the security gateway.

Example 17 includes the base station of any of the Examples 15-16, wherein the tunnel inner address assigned to said base station comprises an Internet Protocol (IP) address assigned by the security gateway.

Example 18 includes the base station of any of the Example 14-17, comprising a controller and at least first radio point located remotely from the controller.

Example 19 includes the base station of any of the Examples 14-18, wherein said base station is configured to determine whether to include the outer address assigned to said base station in the response to the request by determining whether the requesting base station and said base station are in the same cluster.

Example 20 includes the base station of any of the Examples 14-19, wherein the interface is configured to couple the base station to an ETHERNET network.

Example 21 includes the base station of any of the Examples 14-20, wherein said base station is a part of a centralized radio access network (C-RAN).

Example 22 includes the base station of any of the Examples 14-21, wherein said base station is configured to determine whether to include the outer address assigned to said base station in the response to the request by checking whether the requesting base station and said base station are able to communicate with each other using only local communications.

Example 23 includes a base station comprising: an interface to communicatively couple said base station to a network; wherein said base station is configured to perform at least some processing associated with implementing an air interface to provide wireless service; and wherein said base station is configured to: send a request to a replying base station for a transport layer address assigned to the replying base station that is suitable for establishing a base-station-to-base-station connection between said base station and the replying base station; receive a response to the request from the replying base station; determine whether an outer address assigned to the replying base station is included in the response; and in response to determining that the outer address assigned to the replying base station is included in the response, use the outer address assigned to the replying base station to establish the base-station-to-base-station connection between said base station and the replying base station without using the security gateway.

Example 24 includes the base station of Example 23, wherein the base-station-to-base-station connection is used to implement an LTE X2 interface between said base station and the replying base station.

Example 25 includes the base station of Example 24, wherein the outer address assigned to the replying base station comprises an Internet Protocol (IP) address assigned by a Dynamic Host Configuration Protocol (DHCP) server; and wherein said base station is configured to use the IP address assigned to the replying base station by the DHCP server to establish the LTE X2 interface between said base station and the replying base station using an X2 mesh architecture that comprises an Internet Protocol Security (IPSec) connection between said base station and the replying base station without using the security gateway.

Example 26 includes the base station of any of the Examples 23-25, further comprising: wherein said base station is configured to, in response to determining that the outer address assigned to the replying base station is not included in the response, use the tunnel inner address assigned by the security gateway to the replying base station to establish the base-station-to-base-station connection between said base station and the replying base station using the security gateway.

Example 27 includes the base station of Example 26, wherein the base-station-to-base-station connection is used to implement an LTE X2 interface between said base station and the replying base station; wherein the tunnel inner address assigned to the replying base station comprises an Internet Protocol (IP) address assigned by the security gateway; and wherein said base station is configured to, in response to determining that the outer address assigned to the replying base station is not included in the response, use the IP address assigned to the replying base station by the security gateway to establish the LTE X2 interface between said base station and the replying base station using an X2 Star architecture that comprises a first Internet Protocol Security (IPSec) connection established between said base station and the security gateway and a second IPSec connection established between the security gateway and the replying base station.

Example 28 includes the base station of any of the Examples 23-27, further comprising a controller and at least one radio point located remotely from the first controller.

Example 29 includes the base station of any of the Examples 23-28, wherein said base station is configured to determine whether the outer address assigned to the replying base station is included in the response by: determining whether said base station and the replying base station are in the same cluster.

Example 30 includes the base station of any of the Examples 23-29, wherein the interface is configured to couple the base station to an ETHERNET network.

Example 31 includes the base station of any of the Examples 23-30, wherein said base station is a part of a centralized radio access network (C-RAN).

Example 32 includes the base station of any of the Examples 23-31, wherein said base station is configured to determine whether the outer address assigned to the replying base station is included in the response by: checking whether said base station and the replying base station are able to communicate with each other using only local communications.

Example 33 includes the base station of any of the Examples 23-32, wherein said base station is configured to determine whether the outer address assigned to the replying base station is included in the response by: checking the response to determine if the outer address assigned to the replying base station is included in the response.

What is claimed is:

1. A method comprising:
    sending a request from a first base station to a second base station for a transport layer address assigned to the second base station that is suitable for establishing a base-station-to-base-station connection between the first base station and the second base station;
    determining, by the second base station, prior to establishing the base-station-to-base-station connection between the first base station and the second base station, whether to include an outer address assigned to the second base station in a response to the request;
    in response to determining to include the outer address assigned to the second base station in the response, sending, by the second base station, the response to the request to the first base station, the response to the request including a tunnel inner address assigned by a security gateway to the second base station and the outer address assigned to the second base station;
    determining, by the first base station, whether the outer address assigned to the second base station is included in the response; and
    in response to determining that the outer address assigned to the second base station is included in the response, using the outer address assigned to the second base station to establish the base-station-to-base-station connection between the first base station and the second base station without using the security gateway.

2. The method of claim 1, wherein the base-station-to-base-station connection is used to implement an LTE X2 interface between the first base station and the second base station.

3. The method of claim 2, wherein the outer address assigned to the second base station comprises an Internet Protocol (IP) address assigned by a Dynamic Host Configuration Protocol (DHCP) server;
   wherein using the outer address assigned to the second base station to establish the base-station-to-base-station connection between the first base station and the second base station without using the security gateway comprises:
   using the IP address assigned to the second base station by the DHCP server to establish the LTE X2 interface between the first base station and the second base station using an X2 mesh architecture that comprises an Internet Protocol Security (IPSec) connection between the first base station and the second base station without using the security gateway.

4. The method of claim 1, further comprising:
   in response to the second base station determining not to include the outer address assigned to the second base station in the response, sending, by the second base station, the response to the request to the first base station, the response to the request including the tunnel inner address assigned by the security gateway to the second base station; and
   in response to the first base station determining that the outer address assigned to the second base station is not included in the response, using the tunnel inner address assigned to the second base station to establish the base-station-to-base-station connection between the first base station and the second base station using the security gateway.

5. The method of claim 4, wherein the base-station-to-base-station connection is used to implement an LTE X2 interface between the first base station and the second base station;
   wherein the tunnel inner address assigned to the second base station comprises an Internet Protocol (IP) address assigned by the security gateway;
   wherein using the tunnel inner address assigned to the second base station to establish the base-station-to-base-station connection between the first base station and the second base station using the security gateway comprises:
   using the IP address assigned to the second base station by the security gateway to establish the LTE X2 interface between the first base station and the second base station using an X2 Star architecture that comprises a first Internet Protocol Security (IPSec) connection established between the first base station and the security gateway and a second IPSec connection established between the security gateway and the second base station.

6. The method of claim 1, wherein the first base station comprises a first controller and at least one first radio point located remotely from the first controller; and
   wherein the second base station comprises a second controller and at least one second radio point located remotely from the second controller.

7. The method of claim 1, wherein determining, by the second base station, whether to include the outer address assigned to the second base station in the response to the request comprises:
   determining, by the second base station, whether the first base station and the second base station are in a same cluster.

8. The method of claim 1, wherein determining, by the first base station, whether the outer address assigned to the second base station is included in the response comprises:
   determining, by the second base station, whether the first base station and the second base station are in a same cluster.

9. The method of claim 1, wherein the first base station and the second base station are communicatively coupled to one another at least in part by an ETHERNET network.

10. The method of claim 1, wherein the first base station and the second base station are a part of a centralized radio access network (C-RAN).

11. The method of claim 1, wherein determining, by the second base station, whether to include the outer address assigned to the second base station in the response to the request comprises:
   checking whether the first base station and the second base station are able to communicate with each other using only local communications.

12. The method of claim 1, wherein determining, by the first base station, whether the outer address assigned to the second base station is included in the response comprises:
   checking whether the first base station and the second base station are able to communicate with each other using only local communications.

13. The method of claim 1, wherein determining, by the first base station, whether the outer address assigned to the second base station is included in the response comprises:
   checking the response to determine if the outer address assigned to the second base station is included in the response.

14. A base station comprising:
   an interface to communicatively couple said base station to a network;
   wherein said base station is configured to perform at least some processing associated with implementing an air interface to provide wireless service;
   wherein said base station is configured to respond to a request from a requesting base station for a transport layer address assigned to said base station that is suitable for establishing a base-station-to-base-station connection between the requesting base station and said base station by:
      determining, prior to establishing the base-station-to-base-station connection between said base station and the requesting base station, whether to include an outer address assigned to the said base station in a response to the request;
      in response to determining to include the outer address assigned to said base station in the response, sending the response to the request to the requesting base station, the response to the request including a tunnel inner address assigned by a security gateway to said base station and the outer address assigned to said base station; and
   wherein the outer address assigned to said base station is used to establish the base-station-to-base-station connection between said base station and the requesting base station without using the security gateway.

15. The base station of claim 14, wherein the base-station-to-base-station connection is used to implement an LTE X2 interface between said base station and the requesting base station.

16. The base station of claim 15, wherein the outer address assigned to said base station comprises an Internet Protocol (IP) address assigned by a Dynamic Host Configuration Protocol (DHCP) server; and
   wherein the IP address assigned to said base station by the DHCP server is used to establish the LTE X2 interface between the requesting base station and said base station using an X2 mesh architecture that comprises an Internet Protocol Security (IPSec) connection between the requesting base station and said base station without using the security gateway.

17. The base station of claim 15, wherein the tunnel inner address assigned to said base station comprises an Internet Protocol (IP) address assigned by the security gateway.

18. The base station of claim 14, comprising a controller and at least first one radio point located remotely from the controller.

19. The base station of claim 14, wherein said base station is configured to determine whether to include the outer address assigned to said base station in the response to the request by determining whether the requesting base station and said base station are in a same cluster.

20. The base station of claim 14, wherein the interface is configured to couple the base station to an ETHERNET network.

21. The base station of claim 14, wherein said base station is a part of a centralized radio access network (C-RAN).

22. The base station of claim 14, wherein said base station is configured to determine whether to include the outer address assigned to said base station in the response to the request by checking whether the requesting base station and said base station are able to communicate with each other using only local communications.

23. A base station comprising:
an interface to communicatively couple said base station to a network;
wherein said base station is configured to perform at least some processing associated with implementing an air interface to provide wireless service; and
wherein said base station is configured to:
send a request to a replying base station for a transport layer address assigned to the replying base station that is suitable for establishing a base-station-to-base-station connection between said base station and the replying base station;
receive a response to the request from the replying base station;
determine, prior to establishing the base-station-to-base-station connection between said base station and the replying base station, whether an outer address assigned to the replying base station is included in the response; and
in response to determining that the outer address assigned to the replying base station is included in the response, use the outer address assigned to the replying base station to establish the base-station-to-base-station connection between said base station and the replying base station without using a security gateway.

24. The base station of claim 23, wherein the base-station-to-base-station connection is used to implement an LTE X2 interface between said base station and the replying base station.

25. The base station of claim 24, wherein the outer address assigned to the replying base station comprises an Internet Protocol (IP) address assigned by a Dynamic Host Configuration Protocol (DHCP) server; and
wherein said base station is configured to use the IP address assigned to the replying base station by the DHCP server to establish the LTE X2 interface between said base station and the replying base station using an X2 mesh architecture that comprises an Internet Protocol Security (IPSec) connection between said base station and the replying base station without using the security gateway.

26. The base station of claim 23, further comprising:
wherein said base station is configured to, in response to determining that the outer address assigned to the replying base station is not included in the response, use a tunnel inner address assigned by the security gateway to the replying base station to establish the base-station-to-base-station connection between said base station and the replying base station using the security gateway.

27. The base station of claim 26, wherein the base-station-to-base-station connection is used to implement an LTE X2 interface between said base station and the replying base station;
wherein the tunnel inner address assigned to the replying base station comprises an Internet Protocol (IP) address assigned by the security gateway; and
wherein said base station is configured to, in response to determining that the outer address assigned to the replying base station is not included in the response, use the IP address assigned to the replying base station by the security gateway to establish the LTE X2 interface between said base station and the replying base station using an X2 Star architecture that comprises a first Internet Protocol Security (IPSec) connection established between said base station and the security gateway and a second IPSec connection established between the security gateway and the replying base station.

28. The base station of claim 23, further comprising a controller and at least one radio point located remotely from the controller.

29. The base station of claim 23, wherein said base station is configured to determine whether the outer address assigned to the replying base station is included in the response by:
determining whether said base station and the replying base station are in a same cluster.

30. The base station of claim 23, wherein the interface is configured to couple the base station to an ETHERNET network.

31. The base station of claim 23, wherein said base station is a part of a centralized radio access network (C-RAN).

32. The base station of claim 23, wherein said base station is configured to determine whether the outer address assigned to the replying base station is included in the response by:
checking whether said base station and the replying base station are able to communicate with each other using only local communications.

33. The base station of claim 23, wherein said base station is configured to determine whether the outer address assigned to the replying base station is included in the response by:
checking the response to determine if the outer address assigned to the replying base station is included in the response.

* * * * *